US011219722B2

(12) United States Patent
Matsumoto et al.

(10) Patent No.: US 11,219,722 B2
(45) Date of Patent: Jan. 11, 2022

(54) NEEDLE-EQUIPPED OUTER TUBE

(71) Applicant: TERUMO KABUSHIKI KAISHA, Tokyo (JP)

(72) Inventors: Kozo Matsumoto, Nakakoma-gun (JP); Masaaki Kasai, Nakakoma-gun (JP); Tsutomu Sugiki, Nakakoma-gun (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/289,471

(22) Filed: Feb. 28, 2019

(65) Prior Publication Data

US 2019/0192787 A1    Jun. 27, 2019

Related U.S. Application Data

(60) Division of application No. 14/260,965, filed on Apr. 24, 2014, now Pat. No. 10,258,747, which is a continuation of application No. PCT/JP2012/069545, filed on Aug. 1, 2012.

(30) Foreign Application Priority Data

Nov. 2, 2011 (JP) ................................. 2011-241403

(51) Int. Cl.
*A61M 5/34* (2006.01)
*A61M 5/32* (2006.01)

(52) U.S. Cl.
CPC .............. *A61M 5/344* (2013.01); *A61M 5/34* (2013.01); *A61M 5/346* (2013.01); *A61M 5/3202* (2013.01); *A61M 2207/00* (2013.01)

(58) Field of Classification Search
CPC ........ A61M 5/34; A61M 5/344; A61M 5/346; A61M 2005/31516; A61M 2005/3118; A61M 5/2429; A61M 5/283; B29C 65/32; B29C 65/3668; B29C 65/46
See application file for complete search history.

(56) References Cited

U.S. PATENT DOCUMENTS

| 4,390,668 A | 6/1983 | Garver, Sr. |
| 4,468,223 A † | 8/1984 | Minagawa |
| 5,217,025 A | 6/1993 | Okamura |

(Continued)

FOREIGN PATENT DOCUMENTS

| JP | H01-11256 Y2 | 3/1989 |
| JP | H09-276404 A | 10/1997 |

(Continued)

OTHER PUBLICATIONS

International Searching Authority, "International Search Report," issued in connection with International Patent Application No. PCT/JP2012/069545, dated Sep. 18, 2012.
International Searching Authority, "Written Opinion," issued in connection with International Patent Application No. PCT/JP2012/069545, dated Sep. 18, 2012.

(Continued)

*Primary Examiner* — Deanna K Hall
(74) *Attorney, Agent, or Firm* — Foley & Lardner LLP

(57) ABSTRACT

A needle-equipped outer tube includes a needle; a joint member that supports the needle, the needle being insert molded or thermally welded to the joint member; and an outer tube including a connection section, wherein the joint member is thermally welded to the connection section of the outer tube.

7 Claims, 11 Drawing Sheets

(56) References Cited

U.S. PATENT DOCUMENTS

| | | | |
|---|---|---|---|
| 5,810,785 A | | 9/1998 | Bogert et al. |
| 5,964,737 A | * | 10/1999 | Caizza .................. A61M 5/34 |
| | | | 604/187 |
| 2010/0145284 A1 | † | 6/2010 | Togashi |
| 2013/0231617 A1 | * | 9/2013 | Hoppe .................. A61M 5/349 |
| | | | 604/272 |

FOREIGN PATENT DOCUMENTS

| | | | |
|---|---|---|---|
| JP | 2004-154210 A | | 6/2004 |
| JP | 2005-342100 A | | 12/2005 |
| JP | 2005342100 | † | 12/2005 |
| JP | 2006116217 | † | 5/2006 |
| JP | 2008-006050 A | | 1/2008 |
| JP | 2011-011000 A | | 1/2011 |
| JP | 2011011000 | † | 1/2011 |
| WO | WO 2008/139982 A1 | | 11/2008 |

OTHER PUBLICATIONS

Extended European Search Report issued in Application No. 12845780.1 dated Apr. 20, 2015.

English-Language Translation of the First Office Action issued in Chinese Patent Application No. 201280053343.3 dated Sep. 29, 2015.

English-Language Translation of the Second Office Action issued in Chinese Patent Application No. 201280053343.3 dated Jun. 3, 2016.

English-Language Translation of Rejection Decision issued in Chinese Patent Application No. 201280053343.3 dated Dec. 27, 2016.

Communication pursuant to Article 94(3) EPC issued in European Patent Application No. 12 845 780.1 dated Jul. 1, 2016.

English-Language Translation of Notification of Reason for Refusal issued in Japanese Patent Application No. 2013-541656 dated Nov. 17, 2015.

\* cited by examiner
† cited by third party

NEEDLE-EQUIPPED OUTER TUBE

CROSS-REFERENCE TO RELATED APPLICATIONS

This application is a divisional of U.S. patent application Ser. No. 14/260,965, filed on Apr. 24, 2014, which is a continuation application of and claims the benefit of priority from International Patent Application No. PCT/JP2012/069545, filed on Aug. 1, 2012, which is based upon and claims the benefit of priority of Japanese Application No. 2011-241403 filed on Nov. 2, 2011. The contents of these applications are incorporated herein by reference in their entireties.

BACKGROUND

Technical Field

The present disclosure relates to a method for manufacturing a needle-equipped outer tube in which a needle of a syringe is directly joined to a distal end of an outer tube of the syringe in advance, and to the needle-equipped outer tube.

Background Art

Conventionally, in some outer tubes having a small volume used for insulin administration or vaccination, a needle is previously joined to the outer tube. Such a needle-equipped outer tube is manufactured by joining the needle to the distal end of the outer tube with an epoxy adhesive, a UV-curing type adhesive, or the like (see, e.g., Japanese Examined Utility Model Application Publication No. 1-11256 (hereinafter "JP '256")). Further, there is a needle-equipped outer tube manufactured by joining a needle to the distal end of the outer tube by insert molding (see, e.g., PCT Publication No. WO 2008/139982 A (hereinafter "WO '982")).

Besides the above, a prefilled syringe in which a medicine is previously filled in the outer tube is frequently used. Further, a needle-equipped outer tube in which a medicine is previously filled is proposed.

However, in JP '256, in which a needle is joined to the distal end of the outer tube by an adhesive, the adhesive may make contact (liquid contact) with a medicine which is previously filled in the outer tube of the needle-equipped outer tube, which may have a negative effect on the medicine. Therefore, there is a need for a technique to integrally form a needle and an outer tube with a novel joining method not using an adhesive.

Further, in WO '982, in which a needle is joined to the distal end of the outer tube by insert molding, a mechanism for arranging the needle in the cavity of the mold is necessary (e.g., a mechanism for inserting and removing a rod for attachment). Therefore, the molding machine and supplementary equipment thereof needed to manufacture such a device are complex and large.

SUMMARY OF INVENTION

One object of the present invention is to provide a method for manufacturing a needle-equipped outer tube in which a needle is joined to an outer tube with compact equipment and without using an adhesive, and a needle-equipped outer tube manufactured by the method for manufacturing a needle-equipped outer tube.

In one embodiment, a method for manufacturing a needle-equipped outer tube is provided. A needle, a joint member having a needle insertion hole in which the needle can be inserted, and an outer tube provided with a connection section at one of end portions in the axial direction are prepared. Further, the joint member, in which the needle is inserted in the needle insertion hole, engaging with the connection section is pressed toward the connection section by a pressing member, and under this state, the needle and the joint member as well as the joint member and the connection section are thermally welded to manufacture the needle-equipped outer tube.

The method for manufacturing a needle-equipped outer tube includes, for example, an engagement process, an assembling process, and a welding process.

In the engagement process, the joint member engages with the connection section provided at one of end portions in the axial direction of the outer tube.

In the assembling process, the needle is inserted in the needle insertion hole formed in the joint member.

In the welding process, the joint member is pressed along the axial direction of the outer tube by the pressing member, and under this state, the joint member and the needle as well as the joint member and the connection section are thermally welded.

In such method for manufacturing a needle-equipped outer tube, the joint member and the needle as well as the joint member and the connection section of the outer tube are joined by thermal welding, so that the needle is fixed to the outer tube without using an adhesive. Further, since the joint member is pressed along the axial direction of the outer tube during the thermal welding, the thermal welding is carried out with no air existing between the joint member and the connection section of the outer tube. Consequently, foaming in the joint section (thermally welded section) can be prevented, thereby preventing deterioration in aesthetic of the needle-equipped outer tube.

Further, the method for manufacturing a needle-equipped outer tube may include, for example, an insert molding process, an engagement process, and a welding process.

In the insert molding process, the needle and the joint member which supports the needle are integrally formed by insert molding.

In the engagement process, the joint member supporting the needle engages with the connection section provided at the end portion in the axial direction of the outer tube.

In the welding process, the joint member is pressed along the axial direction of the outer tube by the pressing member, and under this state, the joint member and the connection section is thermally welded.

In the method for manufacturing a needle-equipped outer tube as described above, the joint member supporting the needle is joined to the connection section of the outer tube by thermal welding, so that the needle can be fixed to the outer tube without using an adhesive. Further, since the joint member is pressed along the axial direction of the outer tube during the thermal welding, the joint member and the connection section are thermally welded with no air existing between the joint member and the connection section of the outer tube. Consequently, foaming in the joint section (thermally welded section) can be prevented, thereby preventing deterioration in the appearance of the needle-equipped outer tube.

The needle-equipped outer tube according to an embodiment of the present invention includes the needle, the joint member supporting the needle, and the outer tube.

The outer tube includes the connection section which engages with, and is joined to, the joint member.

Further, the joint member engaging with the connection section of the outer tube is pressed along the axial direction of the outer tube, and under this state, the joint member is joined to the connection section by thermal welding.

The needle and the joint member of the needle-equipped outer tube are joined by thermal welding or insert molding. Further, since the joint member and the connection section of the outer tube are joined by thermal welding, the needle is fixed to the outer tube without using an adhesive.

The method for manufacturing a needle-equipped outer tube and the needle-equipped outer tube provide high joint strength without deteriorating the appearance since the boundary surface between the joint member and the connection section becomes uniform and transparent. Further, since the joint member is pressed toward the connection section during the joining process, the air existing between the joint member which is heat melted and the connection section is discharged from the space between the joint member and the connection section. Further, by suitably setting the heating temperature, foaming in the joint member and the connection section (resin) is prevented. As a result, problems such as reduced strength, contamination, and permeation of a medicine caused by the air existing between the joint member and the connection section can be prevented. Further, since the joint member can be made relatively small, equipment for insert molding the needle and the joint member can be downsized.

By the method for manufacturing a needle-equipped outer tube and the needle-equipped outer tube according to embodiments of the present invention, the needle can be joined to the outer tube with compact equipment without using an adhesive.

DETAILED DESCRIPTION

Figure 1:
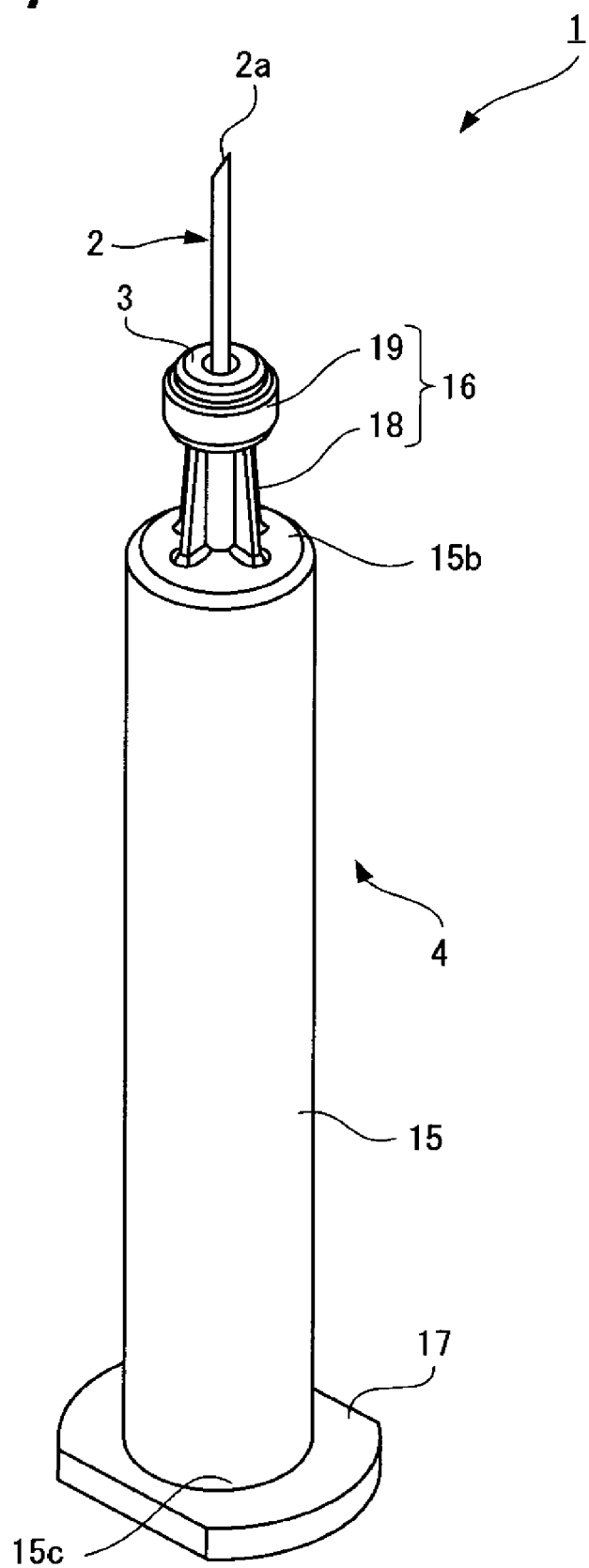
FIG. 1 is a perspective view of a needle-equipped outer tube according to a first embodiment.

The needle-equipped outer tube according to embodiments of the present invention will be described below referring to FIG. 1 to FIG. 15. Note that, in each of the drawings, the same component is indicated with the same reference numeral. Further, the present invention is not limited to the embodiments described below.

Note that, the description will be made in the order listed below.

1. First embodiment of the needle-equipped outer tube
   Configuration of a needle-equipped outer tube
   Method for manufacturing a needle-equipped outer tube
2. Second embodiment of the needle-equipped outer tube
   Configuration of a needle-equipped outer tube
   Method for manufacturing a needle-equipped outer tube
3. Third embodiment of the needle-equipped outer tube
4. Fourth embodiment of the needle-equipped outer tube
5. Fifth embodiment of the needle-equipped outer tube
6. Sixth embodiment of the needle-equipped outer tube
7. Seventh embodiment of the needle-equipped outer tube 1. First Embodiment of the Needle-Equipped Outer Tube <Configuration of a Needle-Equipped Outer Tube>

First, the configuration of the first embodiment of the needle-equipped outer tube will be described referring to FIG. 1 and FIG. 2.

FIG. 1 is a perspective view of the first embodiment of the needle-equipped outer tube. FIG. 2 is an exploded perspective view of the first embodiment of the needle-equipped outer tube.

The needle-equipped outer tube 1 is used to carry out piercing from the surface of a skin with a needle tip so as to inject a medicine into a living body. As illustrated in FIG. 1, the needle-equipped outer tube 1 includes a needle 2, a joint member 3 to which the needle 2 is joined, and an outer tube 4 to which the joint member 3 is joined. Further, a cap 5 (see FIG. 3 and FIG. 4) is attached to the needle-equipped outer tube 1.

[Needle]

First, the needle 2 will be described.

A needle having a gauge size of 10 to 33 (outer diameter of $\phi$ 3.5 to 0.2 mm) according to ISO standards for medical needles (ISO9626:1991/Amd. 1:2001(E)) is used as the needle 2. Preferably, a needle having a gauge size of 16 to 33 (outer diameter of $\phi$ 1.7 to 0.2 mm) is used.

At one of the ends (in the axial direction) of the needle 2, a needle tip 2a which is pierced into a living body is provided. The needle tip 2a has a sharp acute angle forming a bladed edge. Hereinafter, the other end of the needle 2, that is, the end on the side opposite the needle tip 2a, will be referred to as the "proximal end" 2b (see FIG. 2). The needle tip 2a of the needle 2 protrudes from a distal end surface 11a of the joint member 3. The proximal end 2b of the needle 2 protrudes from a rear end surface 12a of the joint member 3. The proximal end 2b of the needle 2 is arranged in a connection section 16 of the outer tube 4.

The middle portion of the needle 2 is inserted in a tubular hole 3a of the joint member 3. The surface of the middle portion of the needle 2 is formed to have a rough surface by applying blasting or the like. In this manner, when the needle 2 and the joint member 3 are joined by thermal welding, the joint strength between the needle 2 and the joint member 3 can be improved by the softened (melted) resin making tight contact with the rough surface of the needle 2. Further, by the softened (melted) resin making tight contact with the rough surface of the needle 2, fluid tightness can be improved. Note that, the surface of the needle 2 may be finished to have a roughness (Ra) of 1.0 to 3.0, preferably, 1.3 to 2.0, by blasting or the like.

As a material of the needle 2, for example, a stainless steel may be used. However, the material is not limited to a stainless steel. Aluminum, an aluminum alloy, titanium, a titanium alloy, or other metals may be used. Further, as for the needle 2, not only a straight needle but also a tapered needle in which at least a portion is tapered can be used. The tapered needle may have a proximal end portion having a diameter larger than that of the end portion of the needle tip 2a, and a middle portion configured as a tapered structure. Further, the cross sectional shape of the needle 2 is not limited to a circle, and may also be a polygon such as a triangle.

Further, to the portion of the surface of the needle 2 close to the needle tip 2a, a coating material composed of, for example, a silicone resin, a fluorine-based resin, or the like is applied. In this manner, the friction between the skin and the needle 2 produced when the needle 2 is pierced into a living body can be reduced, which can ease a pain during the piercing.

[Joint Member]

Now, the joint member 3 will be described.

Figure 2:
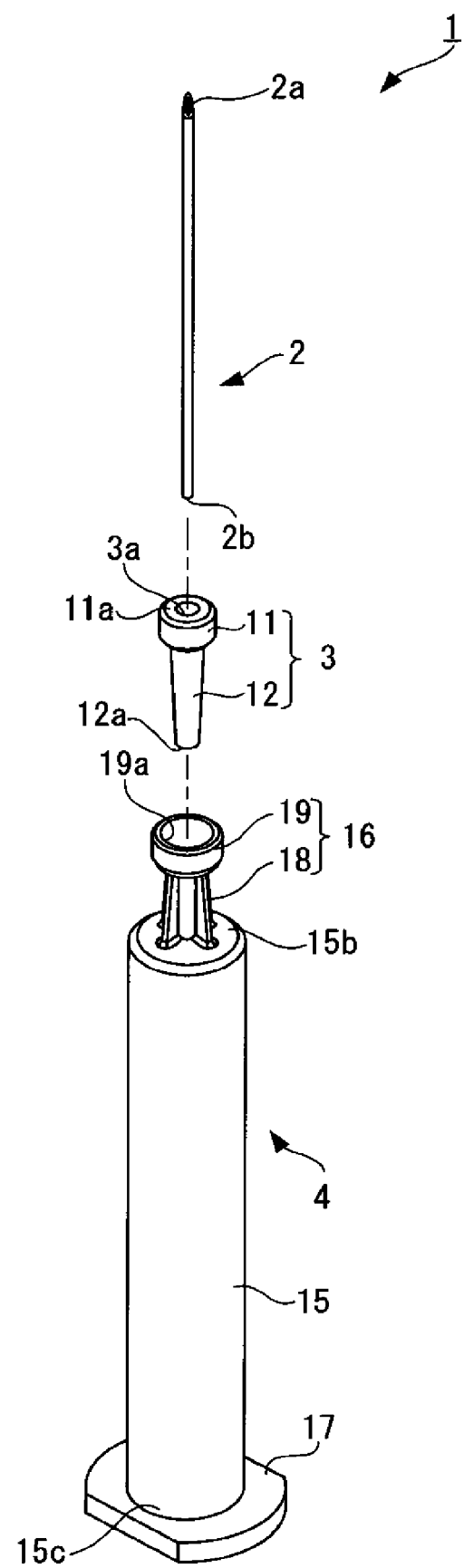
FIG. 2 is an exploded perspective view of the needle-equipped outer tube of the first embodiment.

As illustrated in FIG. 2, the joint member 3 is formed in an approximately cylindrical shape having a tubular hole (needle insertion hole) 3a in which the needle 2 is inserted. The diameter of the tubular hole 3a is provided to be larger than the outer diameter of the needle 2 by about 0.01 to 0.08 mm, preferably, by about 0.01 to 0.03 mm.

The joint member 3 is configured with a distal end side tubular portion 11 and a rear end side tubular portion 12 having an outer diameter smaller than that of the distal end side tubular portion 11.

The distal end side tubular portion 11 is formed in a cylindrical shape having a uniform outer diameter. On the end portion of the distal end side tubular portion 11, opposite to the rear end side tubular portion 12, a distal end surface 11a is formed. The distal end surface 11a is a press force receiving surface which is pressed by a pressing portion 101a of a pressing apparatus 101 which will be described below.

On the end portion of the rear end side tubular portion 12, opposite to the distal end side tubular portion 11, a rear end surface 12a is formed. The rear end side tubular portion 12 is formed in a tapered shape in which the outer diameter gradually decreases toward the rear end surface 12a.

As a material of the joint member 3, various types of resin such as polyvinyl chloride, polyethylene, polypropylene, cyclic polyolefin, polystyrene, poly(4-methylpentene-1), polycarbonate, acrylic resin, acrylonitrile-butadiene-styrene copolymer, polyester such as polyethylene-telephthalate, butadiene-styrene copolymer, and polyamide (e.g., nylon 6, nylon 6,6, nylon 6,10, nylon 12) may be used. Among those, a resin such as polypropylene, cyclic polyolefin, polyester, and poly(4-methylpentene-1) is preferably used. Note that, it is preferable that the material of the joint member 3 is substantially transparent so that the inside of the joint member 3 is visible.

[Outer Tube]

Now, the outer tube 4 will be described.

The outer tube 4 includes an outer tube body 15 in which a medicine is filled and a connection section 16 to which the joint member 3 is joined. The outer tube body 15 is formed in an approximately cylindrical shape having a tubular hole 15a (see FIG. 4). The connection section 16 is provided at an end portion 15b in the axial direction of the outer tube body 15 and a flange 17 is formed on the other end portion 15c.

When the needle-equipped outer tube 1 is used as an ordinary syringe, a pusher and a gasket (not shown in the drawing) are inserted from the other end portion 15c side of the outer tube body 15. Further, when the needle-equipped outer tube 1 is used as a prefilled outer tube, a pusher and a gasket are inserted from the other end portion 15c side after a medicine is filled in the tubular hole 15a of the outer tube body 15.

A medicine to be filled in the tubular hole 15a of the outer tube body 15 may be any medicine which is usually used as an injection, for example, a protein drug such as an antibody, a peptide pharmaceutical such as a hormone, a nucleic acid medicine, a cellular medicine, a blood product, a vaccine for preventing infections, an anticancer agent, an anesthetic, a drug, an antibiotic, a steroid, a proteolytic enzyme inhibitor, a heparin, a saccharide injection such as a glucose, an injection for correcting electrolyte imbalance such as sodium chloride and potassium lactate, a vitamin compound, a fat emulsion, a contrast media, and a stimulant.

Note that, in the embodiment, description is made for an example in which the shape of the outer tube body 15 is formed in an approximately cylindrical shape, though the shape of the outer tube body 15 may be a hollow quadrangular prism shape or a hexagonal prism shape.

The connection section 16 is configured with a tapered engagement portion 18 which is continued to the end portion 15b of the outer tube body 15 and a distal end side engagement portion 19 which is continued to the tapered engagement portion 18.

Figure 4:
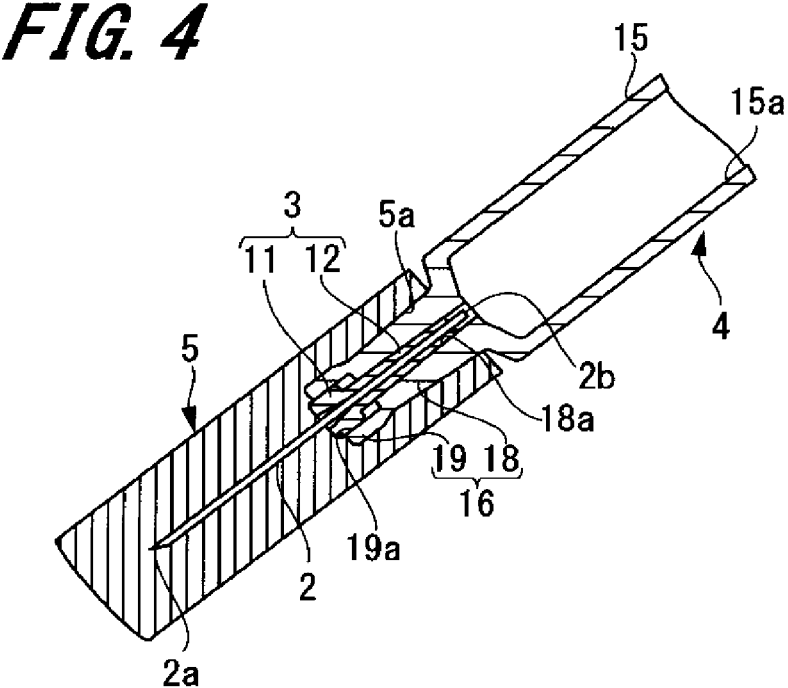
FIG. 4 is a cross sectional view of the needle-equipped outer tube and the cap illustrated in FIG. 3.
Figure 5:
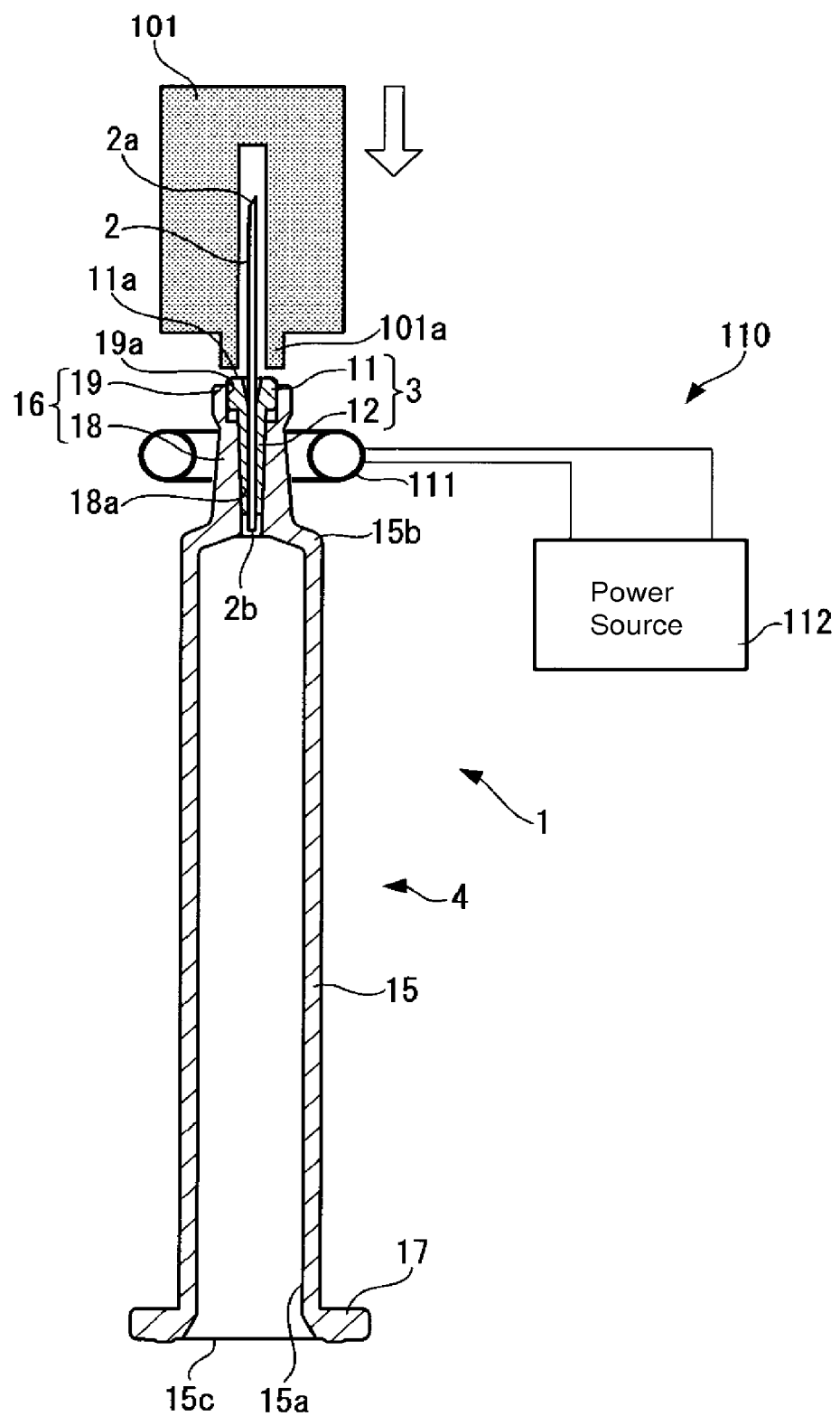
FIG. 5 is an explanatory drawing explaining a method for manufacturing the needle-equipped outer tube of the first embodiment.

The tapered engagement portion 18 has an approximately cross-shaped cross section in a plane perpendicular to the axial direction of the outer tube 4, and an engagement hole 18a having a circular cross section (see FIG. 4 and FIG. 5). The engagement hole 18a is formed in a tapered shape (tapered inner shape) in which the diameter gradually decreases toward the end portion 15b of the outer tube body 15. The rear end side tubular portion 12 of the joint member 3 is inserted in the engagement hole 18a.

The rear end side tubular portion 12 is formed in a tapered shape (tapered outer shape) so as to engage with the engagement hole 18a. Further, taper angles of the engagement hole 18a and the rear end side tubular portion 12 are not particularly limited, though an angle of 1 to 3 degrees is preferable.

Figure 3:
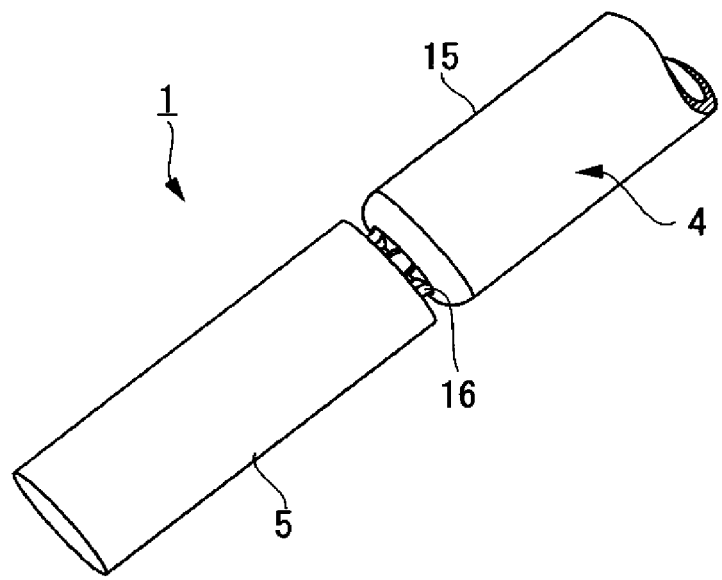
FIG. 3 is a perspective view illustrating a state in which a cap is attached to the needle-equipped outer tube of the first embodiment.

The distal end side engagement portion 19 has an approximately circular cross section in a plane perpendicular to the axial direction of the outer tube 4, and an engagement hole 19a (see FIG. 3). The distal end side tubular portion 11 of the joint member 3 is inserted in the engagement hole 19a. Note that, the diameter of the engagement hole 19a is approximately the same as the outer diameter of the distal end side tubular portion 11 of the joint member 3.

As a material of the outer tube 4 configured with the connection section 16 and the outer tube body 15, a resin similar to that used for the joint member 3 is preferably used. Note that, it is preferable that the material of the outer tube 4 is substantially transparent so that the inside of the outer tube 4 is visible.

Further, the connection section 16 of the outer tube 4 and the joint member 3 are joined by thermal welding. Therefore, it is preferable that the material of the outer tube 4 is substantially the same as the material of the joint member 3. In this manner, preferable bondability between the connection section 16 and the joint member 3 can be obtained so that the connection section 16 and the joint member 3 can firmly be fixed. Further, the welded portion between the connection section 16 and the joint member 3 can be made inconspicuous so that aesthetic of the needle-equipped outer tube 1 can be improved.

[Cap]

Now the cap 5 will be described referring to FIG. 3 and FIG. 4.

FIG. 3 is a perspective view illustrating a state in which the cap 5 is attached to the needle-equipped outer tube 1. FIG. 4 is a cross sectional view illustrating the needle-equipped outer tube 1 and the cap 5 illustrated in FIG. 3.

As illustrated in FIG. 3 and FIG. 4, the cap 5 is formed in an approximately cylindrical shape with one end in the axial direction opened and the other end in the axial direction closed. The cap 5 is formed of a flexible member, for example, a rubber or an elastomer.

The cap 5 is attached to the connection section 16 of the outer tube 4 so as to cover the needle tip 2*a* of the needle 2 and the connection section 16 of the outer tube 4. Further, as illustrated in FIG. 4, a portion of the needle 2 in the needle tip 2*a* side and the connection section 16 are inserted into the tubular hole 5*a* of the cap 5.

Note that, the inner diameter of the tubular hole 5*a* of the cap 5 is provided to be approximately the same as, or slightly smaller than, the outer diameter of the distal end side engagement portion 19 of the connection section 16. Therefore, when the cap 5 is attached to the connection section 16, the outer circumferential surface of the distal end side engagement portion 19 makes tight contact with the inner circumferential surface of the cap 5. In this manner, the space around the needle 2 protruding from the joint member 3 is sealed by the distal end side engagement portion 19 and the inner circumferential surface of the cap 5. As a result, adhering of germs to the needle tip 2*a* can be prevented.

Further, the inner circumferential surface of the cap 5 compresses the boundary portion (narrow portion) between the distal end side engagement portion 19 and the tapered engagement portion 18 of the connection section 16 by the elastic force of the cap 5. In this manner, the inner circumferential surface of the cap 5 and the narrow portion of the connection section 16 engage with each other, thereby preventing the cap 5 from coming off from the connection section 16 (outer tube 4) during transportation.

<Method for Manufacturing a Needle-Equipped Outer Tube>

Now, a method for manufacturing the needle-equipped outer tube 1 will be described referring to FIG. 5 and FIG. 6.

FIG. 5 is an explanatory drawing explaining the method for manufacturing the needle-equipped outer tube 1. FIG. 6 is a cross sectional view illustrating a needle stopping portion of the needle-equipped outer tube 1.

When manufacturing the needle-equipped outer tube 1, at first, each of the needle 2, the joint member 3 and the outer tube 4 is prepared. The needle 2 is formed in a desired tubular body by, for example, press working of a metal plate or swaging process of a hollow pipe. Each of the joint member 3 and the outer tube 4 is formed by injection molding. By separately forming the joint member 3 and the outer tube 4 in this manner, a mold can be made small and simple.

[Engagement Process]

Next, an engagement process is carried out. In the engagement process, the joint member 3 is inserted into the engagement holes 18*a* and 19*a* of the connection section 16 of the outer tube 4. In this manner, the rear end side tubular portion 12 of the joint member 3 engages with the tapered engagement portion 18 of the connection section 16, and at the same time, the distal end side tubular portion 11 of the joint member 3 engages with the distal end side engagement portion 19 of the connection section 16.

[Assembling Process]

Next, the assembling process will be carried out. In the assembling process, the needle 2 is inserted in the tubular hole 3*a* of the joint member 3. In the process, the proximal end 2*b* of the needle 2 makes contact with a needle stopping portion 21 provided in the connection section 16 of the outer tube 4 (see FIG. 6). In this manner, the needle 2 is positioned against the joint member 3 and the outer tube 4 and the proximal end 2*b* of the needle 2 is arranged in the connection section 16. In other words, the proximal end 2*b* of the needle 2 is not arranged in the tubular hole 15*a* of the outer tube body 15. Consequently, the dead volume in the outer tube 4 can be reduced, thereby reducing the amount of medicine remaining in the outer tube 4.

Figure 6:
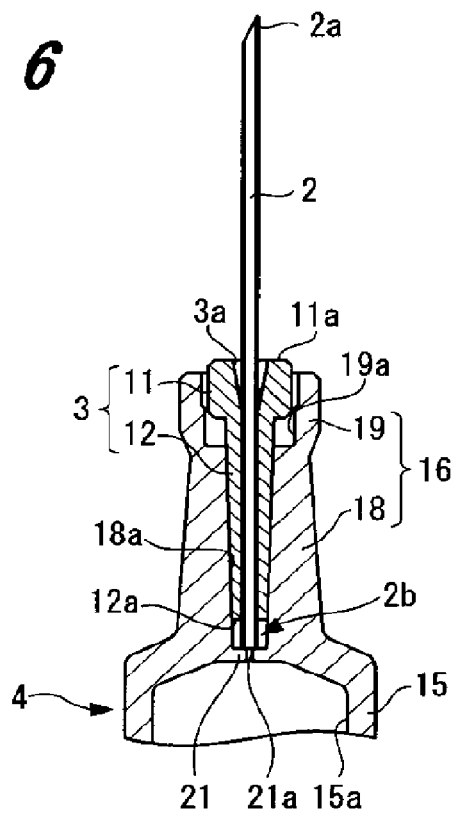
FIG. 6 is a cross sectional view illustrating a needle stopping portion of the needle-equipped outer tube of the first embodiment.

As illustrated in FIG. 6, the needle stopping portion 21 is formed in a ring shaped protrusion which protrudes from the inner surface of the tapered engagement portion 18. A communication hole 21*a* provided in the center of the needle stopping portion 21 makes communication between the tubular hole 15*a* of the outer tube body 15 and engagement holes 18*a* and 19*a* of the connection section 16. Therefore, a needle hole of the needle 2 which is positioned by making contact with the needle stopping portion 21 communicates with the tubular hole 15*a* of the outer tube body 15 via the communication hole 21*a*.

For example, when a 27G needle is applied as the needle 2, the outer diameter of the needle 2 is ϕ 0.41 mm and the inner diameter is ϕ 0.19 to 0.25 mm. In this case, the diameter of the communication hole 21*a* of the needle stopping portion 21 is preferably be ϕ 0.26 to 0.4 mm.

[Welding Process]

Next, a welding process is carried out. In the welding process, the distal end surface 11*a* of the joint member 3 is pressed along the axial direction of the outer tube 4 by the pressing apparatus 101, and under this state, the joint member 3 and the needle 2 as well as the joint member 3 and the connection section 16 of the outer tube 4 are joined by thermal welding.

The pressing apparatus 101 includes a pressing portion 101*a* which presses the distal end surface 11*a* of the joint member 3. By applying pressure to the joint member 3 by the pressing portion 101*a*, the outer circumferential surface of the rear end side tubular portion 12 and the inner circumferential surface of the tapered engagement portion 18 can be kept in tight contact with each other.

In the embodiment, the thermal welding is carried out using a high frequency induction heating apparatus 110. The high frequency induction heating apparatus 110 includes a work coil 111 and a power source 112 which supplies an AC current to the work coil 111.

When the power source 112 supplies an AC current to the work coil 111, a magnetic field is generated around the work coil 111 and an eddy current is produced in the needle 2. Therefore, the temperature of the needle 2 rises to heat the joint member 3. Then the joint member 3 softens to adhere to the needle 2 and the connection section 16 of the outer tube 4. As a result, the joint member 3 and the needle 2 as well as the joint member 3 and the connection section 16 of the outer tube 4 are joined by thermal welding and thereby, the needle-equipped outer tube 1 is manufactured.

Note that, when the thickness of the joint member 3 is provided to be 0.4 to 0.55 mm, it is preferable to set the output of the power source 112 to be 46 to 52 V with 2.5 to 3.2 A and the oscillation period of the work coil 111 to be 4 to 10 seconds (s). Further, the pressing force applied to the joint member 3 is preferably set to be 50 to 100 N.

The condition mentioned above is the case where cyclic olefin polymer (COP) being cyclic polyolefin is used as the material of the joint member, though a condition should be determined to give a suitable resin temperature according to the characteristic of the resin to be used, so as to prevent occurring of foaming, a burnt resin, and deformation.

In the embodiment, since the joint member 3 and the needle 2 as well as the joint member 3 and the outer tube 4 are joined using the high frequency induction heating apparatus 110, the needle 2 is fixed to the outer tube 4 without using an adhesive.

Further, in the embodiment, since the thermal welding is carried out with the joint member 3 pressed along the axial direction of the outer tube 4 by the pressing apparatus 101, no gap is produced between the joint member 3 and the connection section 16 of the outer tube 4. In this manner, foaming will not occur in the joint member 3 when the joint member 3 is heated. As a result, transparency is provided to the joint section without deteriorating aesthetic, and at the same time, the joint member 3 and the needle 2 as well as the joint member 3 and the connection section 16 of the outer tube 4 can tightly be fixed.

Further, since the surface of the portion, inserted in the joint member 3, of the needle 2 is formed in a rough surface by blasting or the like, the softened resin (joint member 3) makes tight contact with the rough surface of the needle 2. As a result, joint strength as well as fluid tightness between the needle 2 and the joint member 3 can be improved.

Further, since the insert molding is not used in the embodiment, a complex and large insert molding apparatus is not necessary so that an excellent needle-equipped outer tube can be manufactured with low cost.

[Comparative Experiment]

Now, the description will be made for a comparative experiment in which cases with and without pressing of the joint member 3 in the welding process using the high frequency induction heating apparatus 110 are compared.

The work coil 111 having an average wire diameter of ϕ 4.3 mm and an average coil inner diameter of ϕ 9 mm is used. The power source 112 is set to output 5 kW with 2 MHz. Further, the work coil is positioned in the middle of the joining section, specifically, in a location 5 to 6 mm from the distal end (distal end side engagement portion 19 side) of the connection section 16. The needle 2 of 27G is used and the thickness of the joint member 3 is provided to be 0.47 mm. Further, taper angles of the engagement hole 18a and the rear end side tubular portion 12 are provided to be 1.6 degrees.

The experiment is evaluated by "external appearance" and "joint strength". The "external appearance" is evaluated to be good (○) when there is no foaming or burning and the length of the welded section is 2 mm or more. Further, "joint strength" is expressed by force (N) required to remove the joint member 3 from the connection section 16 of the outer tube 4. It is sufficient to have the "joint strength" of 50 N or higher, preferably, 80 to 120 N.

The result of the comparative experiment is shown in Table 1.

TABLE 1

| | Welding condition | | | | Result of welding | |
|---|---|---|---|---|---|---|
| | High frequency output | | | Welding | External | Joint |
| | Voltage (V) | Current (A) | Time (sec) | pressure (N) | appearance | strength (N) |
| Example 1 | 52 | 3.2 | 4 | 60 | ○ | 110 |
| Example 2 | 46 | 2.5 | 10 | 60 | ○ | 110 |
| Comparative example 1 | 52 | 3.2 | 4 | 0 | X (Foaming) | 50 |

As shown in Table 1, evaluations of "external appearance" for Example 1 and Example 2 which include pressing of the joint member 3 are good (○). And "joint strength" is 110 N.

Contrarily, for Comparative example 1 which doesn't include pressing of the joint member 3, the evaluation of "external appearance" is not good (x) since foaming occurred in the welded portion. And "joint strength" is 50 N.

According to the comparative experiment, the case in which thermal welding is carried out with the joint member 3 pressed resulted in better "external appearance" and higher "joint strength" than the case in which the joint member 3 is not pressed. Note that, it can be understood that in Comparative example 1, the foaming occurred in the welded portion resulting in reduction of the length of the welded portion to be less than 2 mm, thereby reducing "joint strength".

[Exemplary Modification]

As illustrated in FIG. 6, in the embodiment, the proximal end 2b of the needle 2 is made to contact the needle stopping portion 21 of the outer tube 4 to position the needle 2 during the assembling process. However, the positioning of the needle 2 is not limited to the manner using the needle stopping portion 21, and may be carried out by, for example, a member other than the needle-equipped outer tube 1.

Figure 7:
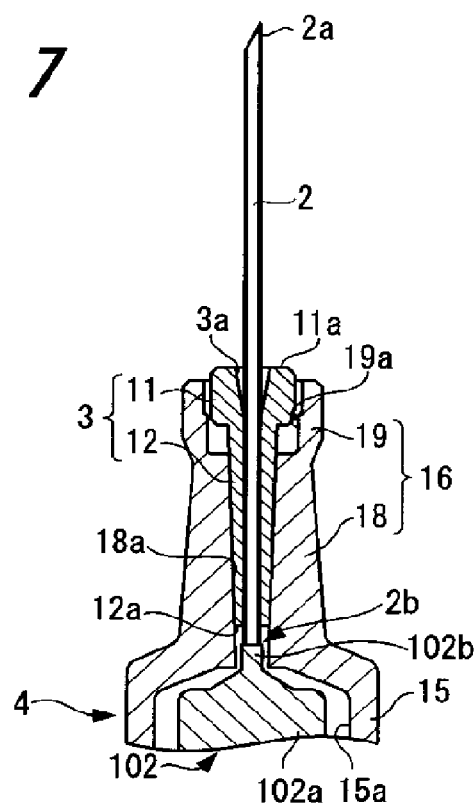
FIG. 7 is a cross sectional view illustrating a needle supporting portion used in the method for manufacturing a needle-equipped outer tube.

FIG. 7 is a cross sectional view illustrating a needle supporting member used in the method for manufacturing a needle-equipped outer tube of the present invention.

As illustrated in FIG. 7, the needle supporting member 102 includes a base portion 102a arranged in the tubular hole 15a of the outer tube body 15 and a support protrusion 102b which protrudes from the upper end of the base portion 102a and supports the proximal end 2b of the needle 2.

The support protrusion 102b of the needle supporting member 102 is inserted in the engagement hole 18a of the connection section 16. Therefore, the proximal end 2b of the needle 2 supported by the support protrusion 102b is arranged in the connection section 16. In other words, the needle 2 is not arranged in the tubular hole 15a of the outer tube body 15. Consequently, the dead volume in the outer tube 4 can be reduced, thereby reducing the amount of medicine remaining in the outer tube 4.

Further, as for an exemplary modification for minimizing the dead volume, the distal end of the needle supporting member 102 may be formed flat so as to block the engagement hole 18a of the connection section 18.

2. Second Embodiment of the Needle-Equipped Outer Tube

<Configuration of a Needle-Equipped Outer Tube>

Now, the second embodiment of the needle-equipped outer tube will be described referring to FIG. 8 and FIG. 9.

Figure 8:
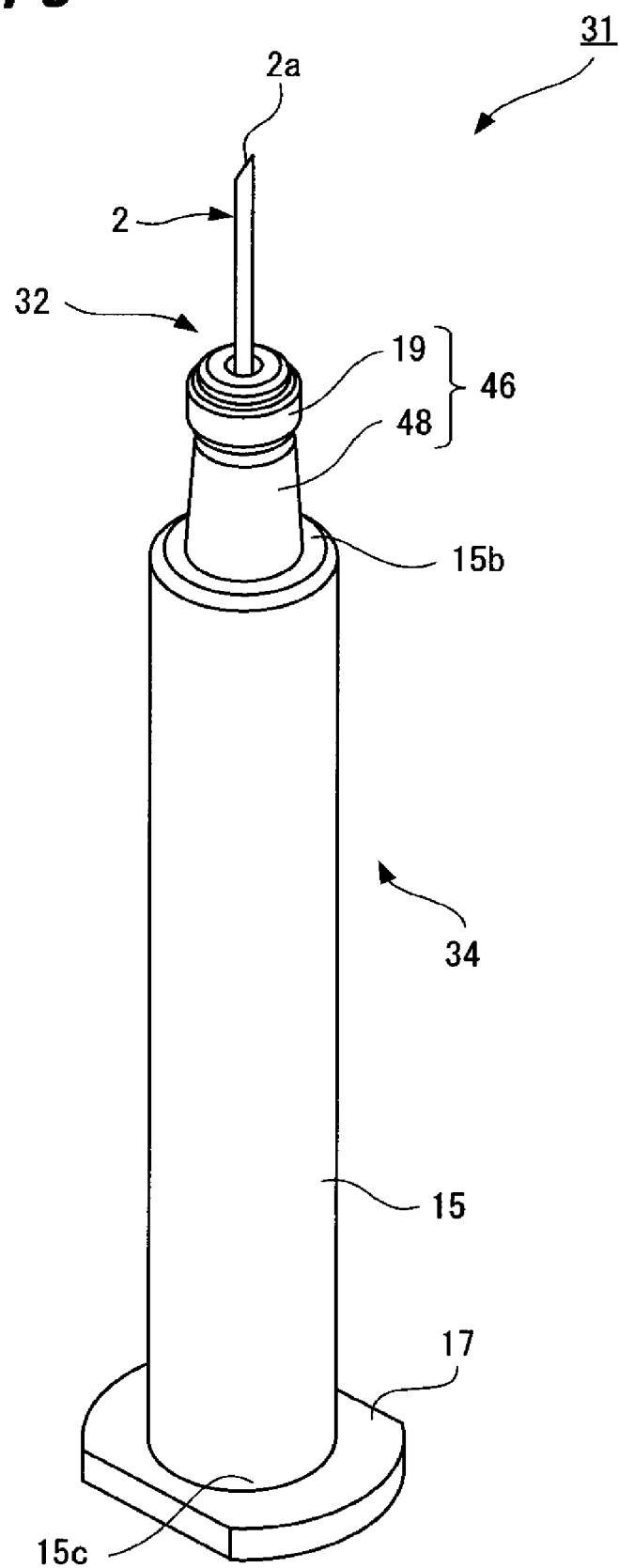
FIG. 8 is a perspective view of a needle-equipped outer tube according to a second embodiment.

FIG. 8 is a perspective view of the second embodiment of the needle-equipped outer tube. FIG. 9 is an exploded perspective view of the second embodiment of the needle-equipped outer tube.

A needle-equipped outer tube 31 has a configuration similar to that of the needle-equipped outer tube 1 of the first embodiment (see FIG. 1). The needle-equipped outer tube 31 is different from the needle-equipped outer tube 1 in that the needle 2 and the joint member 3 are integrally formed in advance by insert molding, and in the shape of an outer tube 34.

Figure 9:
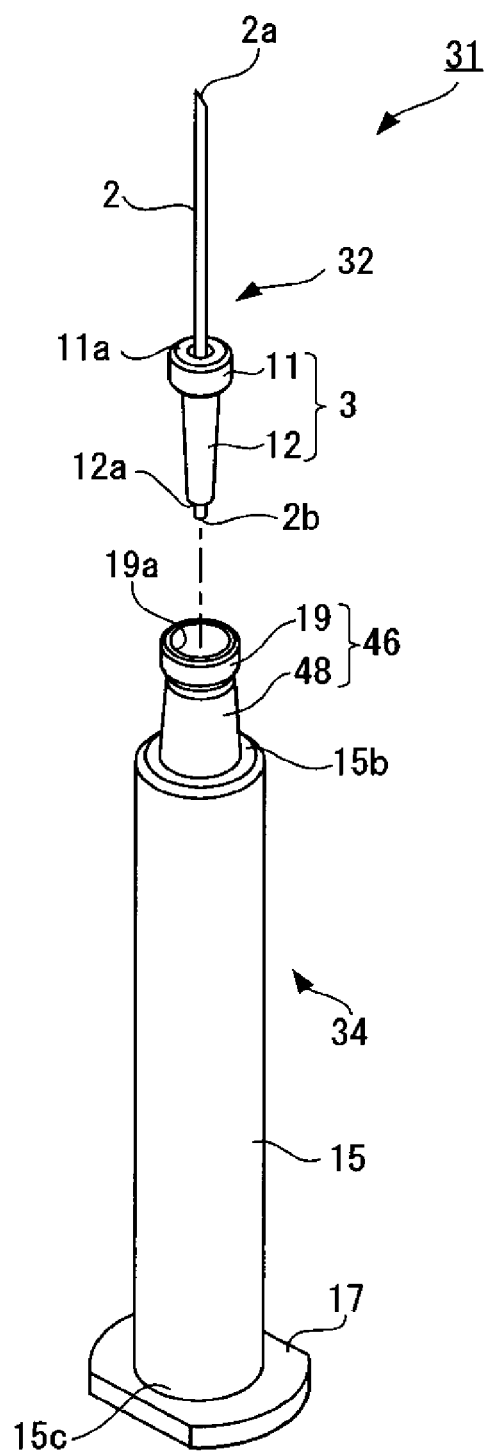
FIG. 9 is an exploded perspective view of needle-equipped outer tube of the second embodiment.

As illustrated in FIG. 8 and FIG. 9, the needle-equipped outer tube 31 includes a needle block 32 and the outer tube 34 to which the needle block 32 is joined. Further, the cap 5 (see FIG. 3 and FIG. 4) is attached to the needle-equipped outer tube 31.

[Needle Block]

Now, the needle block 32 will be described.

The needle block 32 includes the needle 2 and the joint member 3 which supports the needle 2. The needle 2 and the joint member 3 are integrally formed by insert molding.

The needle tip 2a of the needle 2 of the needle block 32 protrudes from the distal end surface 11a of the joint member 3, and the proximal end 2b of the needle 2 protrudes from the rear end surface 12a of the joint member 3 and is arranged in a connection section 46, which will be described below, of the outer tube 34. The distance from the rear end surface 12a of the joint member 3 to the proximal end 2b of the needle 2 is determined so as the proximal end 2b of the needle 2 not to be inserted in the tubular hole 15a (see FIG. 10) of the outer tube body 15 of the outer tube 34.

[Outer Tube]

Next, the outer tube 34 will be described.

The outer tube 34 includes the outer tube body 15 in which a medicine is filled and the connection section 46 to which the joint member 3 of the needle block 32 is joined.

The connection section 46 is configured with a tapered engagement portion 48 which is continued to the end portion 15b of the outer tube body 15 and the distal end side engagement portion 19 which is continued to the tapered engagement portion 48.

The tapered engagement portion 48 is formed in a truncated conical shape. The diameter of the tapered engagement portion 48 gradually decreases toward the distal end side engagement portion 19. Therefore, the tapered engagement portion 48 is formed so as that the cross section perpendicular to the axial direction of the outer tube 34 is a near circle.

Further, the tapered engagement portion 48 includes an engagement hole 48a which communicates with the engagement hole 19a of the distal end side engagement portion 19. The engagement hole 48a is formed in a tapered shape (tapered inner shape) in which the diameter gradually decreases toward the end portion 15b of the outer tube body 15. The rear end side tubular portion 12 of the joint member 3 is inserted in the engagement hole 48a.

The rear end side tubular portion 12 is formed in a tapered shape (tapered outer shape) so as to engage with the engagement hole 48a. Further, taper angles of the engagement hole 48a and the rear end side tubular portion 12 are not particularly limited, though angle of 1 to 3 degrees is preferable.

Conventionally, a connection section of an outer tube and a needle are integrally formed by insert molding. In a case of carrying out injection molding (insert molding), a shrink mark is likely to occur in a thick region. Therefore, when the connection section of the outer tube and the needle are integrally formed by insert molding, the cross section is made, for example, in a cross-shape, so as to restrain the thickness of the connection section.

However, in the needle-equipped outer tube according to the present invention, the portion which supports the needle is formed by joining the connection section of the outer tube and a joint member provided separately from the connection section. Therefore, the thickness of the tapered engagement portion 48 of the connection section 46 of the embodiment of the present invention is restrained even when the tapered engagement portion 48 has a conical shape (column shape). Consequently, even when the tapered engagement portion 48 has a conical shape (column shape), generation of a shrink mark can be prevented or restrained.

In the embodiment, the cap 5 (see FIG. 4) can be made to tightly contact the tapered engagement portion 48 since the tapered engagement portion 48 is provided in a conical shape (column shape). As a result, sealability in the cap 5 can be provided so that the inside of the cap 5 can be kept clean. Further, the cap 5 is further securely assembled, since the cap 5 (see FIG. 4) tightly contacts the tapered engagement portion 48.

<Method for Manufacturing a Needle-Equipped Outer Tube>

Next, the method for manufacturing the needle-equipped outer tube 31 will be described referring to FIG. 10.

Figure 10:
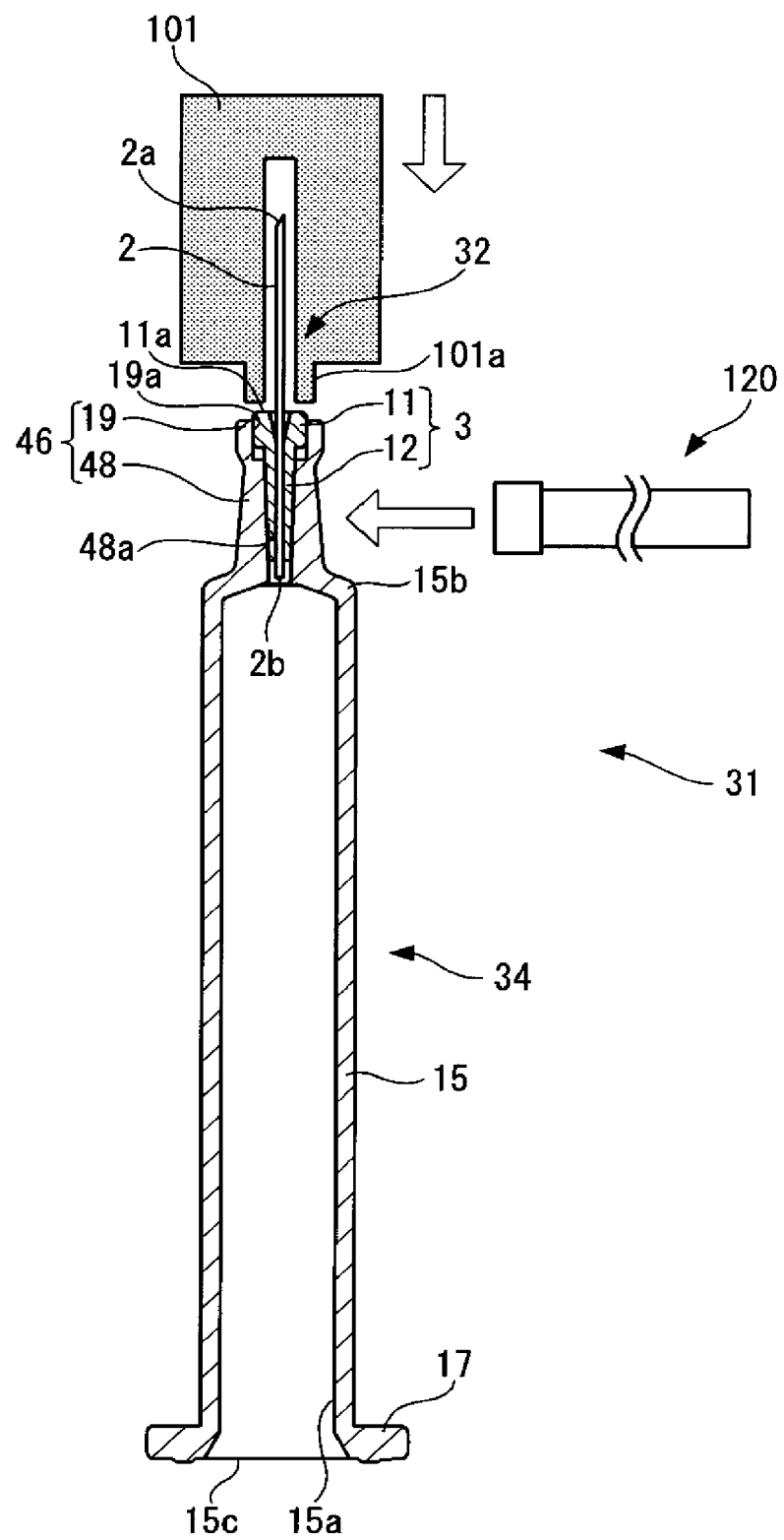
FIG. 10 is an explanatory drawing explaining a method for manufacturing the needle-equipped outer tube of the second embodiment.

FIG. 10 is an explanatory drawing explaining the method for manufacturing the needle-equipped outer tube 1.

When the needle-equipped outer tube 31 is manufactured, firstly, the needle 2 and the outer tube 34 are prepared. The needle 2 is formed in a desired tubular body by, for example, press working of a metal plate or swaging process of a hollow pipe. The outer tube 34 is formed by, for example, injection molding.

[Insert Molding Process]

Next, the insert molding process will be described. In the insert molding process, the needle 2 and the joint member 3 are integrally formed by insert molding. Thereby, the needle block 32 is manufactured. Since the needle block 32 and the outer tube 34 are separately molded in this manner, a mold and a molding apparatus can be downsized.

[Engagement Process]

Next, an engagement process is carried out. In the engagement process, the joint member 3 of the needle block 32 is inserted in the engagement holes 48a and 19a of the connection section 46 of the outer tube 4. In this manner, the rear end side tubular portion 12 of the joint member 3 engages with the tapered engagement portion 48 of the connection section 46 and at the same time, the distal end side tubular portion 11 of the joint member 3 engages with the distal end side engagement portion 19 of the connection section 46.

Thereby, the needle 2 of the needle block 32 is positioned against the outer tube 34 and the proximal end 2b of the needle 2 is arranged in the connection section 46. In other words, the proximal end 2b of the needle 2 is not arranged in the tubular hole 15a of the outer tube body 15. As a result, the dead volume in the outer tube 34 can be reduced, thereby reducing the amount of medicine remaining in the outer tube 34.

[Welding Process]

Next, a welding process is carried out. In the welding process, the distal end surface 11a of the joint member 3 is pressed along the axial direction of the outer tube 34 by the pressing apparatus 101, and under this state, the joint member 3 of the needle block 32 and the connection section 16 of the outer tube 34 are joined by thermal welding.

By applying pressure to the joint member 3 by the pressing portion 101a of the pressing apparatus 101, the outer circumferential surface of the rear end side tubular portion 12 and the inner circumferential surface of the tapered engagement portion 48 can be kept in tight contact with each other.

In the embodiment, a semiconductor laser irradiation apparatus 120 is used to carry out thermal welding. The joint section of the needle 2 of the needle block 32 is irradiated with a laser by the semiconductor laser irradiation apparatus 120. Therefore, the temperature of the needle 2 rises to heat the joint member 3. Then, the joint member 3 softens to adhere to the needle 2 and the connection section 46 of the outer tube 34. As a result, the joint member 3 and the needle 2 as well as the joint member 3 and the connection section 46 of the outer tube 34 are joined by thermal welding and thereby, the needle-equipped outer tube 31 is manufactured.

Note that, when the thickness of the joint member 3 is provided to be 0.4 to 0.55 mm, it is preferable to set the output of the semiconductor laser irradiation apparatus 120 to be 15 to 25 W and the irradiation time of a laser to be 1.5 to 3 seconds (s). Further, as for an optical system, a focus diameter is preferably set to be φ 2.5 to 4 mm. Further, the pressing force applied to the joint member 3 is preferably set to be 50 to 100 N.

The condition mentioned above is the case where cyclic olefin polymer (COP) being cyclic polyolefin is used as the material of the joint member, though a condition should be determined to give a suitable resin temperature according to the characteristic of the resin to be used, so as to prevent occurring of foaming, a burnt resin, and deformation.

In the embodiment, since the joint member 3 and the needle 2 as well as the joint member 3 and the outer tube 34 are joined by using the semiconductor laser irradiation apparatus 120, the needle 2 is fixed to the outer tube 34 without using an adhesive.

Further, in the embodiment, since the thermal welding is carried out with the joint member 3 pressed along the axial direction of the outer tube 34 by the pressing apparatus 101, no gap is produced between the joint member 3 and the connection section 46 of the outer tube 34. In this manner, foaming will not occur in the joint member 3 when the joint member 3 is heated. As a result, transparency is provided to the joint section without deteriorating aesthetic, and at the same time, the joint member 3 and the needle 2 as well as the joint member 3 and the connection section 46 of the outer tube 34 can tightly be fixed.

Further, regarding the injection molding of the outer tube, since the piece formed by injection molding is far smaller than the piece made by directly forming the needle on the outer tube by insert molding, the molding apparatus can be downsized, thereby reducing the cost of facility.

[Comparative Experiment]

Next, the description will be made for a comparative experiment in which cases with and without pressing of the joint member 3 in the welding process using the semiconductor laser irradiation apparatus 120 are compared.

The output of the semiconductor laser irradiation apparatus 120 is set to be 15 W or 20 W. The irradiation time of a laser is set to be 1.5 to 3 seconds. Further, the focus diameter of the semiconductor laser irradiation apparatus 120 is set to be φ 3 mm for every case. The location which is irradiated with a laser is set in the middle of the joint section, specifically, 5 to 6 mm from the distal end (distal end side engagement portion 19 side) of the connection section 16. The needle 2 of 27G is used and the thickness of the joint member 3 is provided to be 0.47 mm.

The experiment is evaluated by "external appearance" and "joint strength". The "external appearance" is evaluated to be good (○) when there is no foaming or burning and the length of the welded section is 2 mm or more. Further, "joint strength" is expressed by force (N) required to remove the joint member 3 from the connection section 46 of the outer tube 34. It is sufficient to have the "joint strength" of 50 N or higher, preferably, 80 to 120 N.

The result of the comparative experiment is illustrated in Table 2.

TABLE 2

| | Welding condition | | | Result of welding | |
|---|---|---|---|---|---|
| | Laser output | | Welding | | |
| | Energy (W) | Time (sec) | pressure (N) | External appearance | Joint strength (N) |
| Example 3 | 20 | 1.5 | 80 | ○ | 115 |
| Example 4 | 20 | 2 | 80 | ○ | 120 |
| Example 5 | 15 | 3 | 80 | ○ | 120 |
| Comparative example 2 | 20 | 1.5 | 0 | X (Foaming) | 60 |

As shown in Table 2, evaluations of "external appearance" for Example 3, Example 4, and Example 5 which include pressing of the joint member 3 are good (○). And "joint strength" is 115 to 120 N.

Contrarily, for Comparative example 2 which doesn't include pressing of the joint member 3, the evaluation of "external appearance" is not good (x) since foaming occurred in the welded portion. And joint strength between the joint member 3 and the connection section 46 of the outer tube 34 is 60 N.

According to the comparative experiment, the case in which thermal welding is carried out with the joint member 3 pressed resulted in better "external appearance" than the case in which the joint member 3 is not pressed. Further, in the case when thermal welding is carried out with the joint member 3 pressed, it is confirmed that the joint member 3 and the connection section 46 of the outer tube 34 are firmly joined. Note that, it can be understood that in Comparative example 2, the foaming occurred in the welded portion resulting in reduction of the length of the welded portion, thereby reducing joint strength between the joint member 3 and the outer tube 34.

3. Third Embodiment of the Needle-Equipped Outer Tube

<Configuration of a Needle-Equipped Outer Tube>

Figure 11:
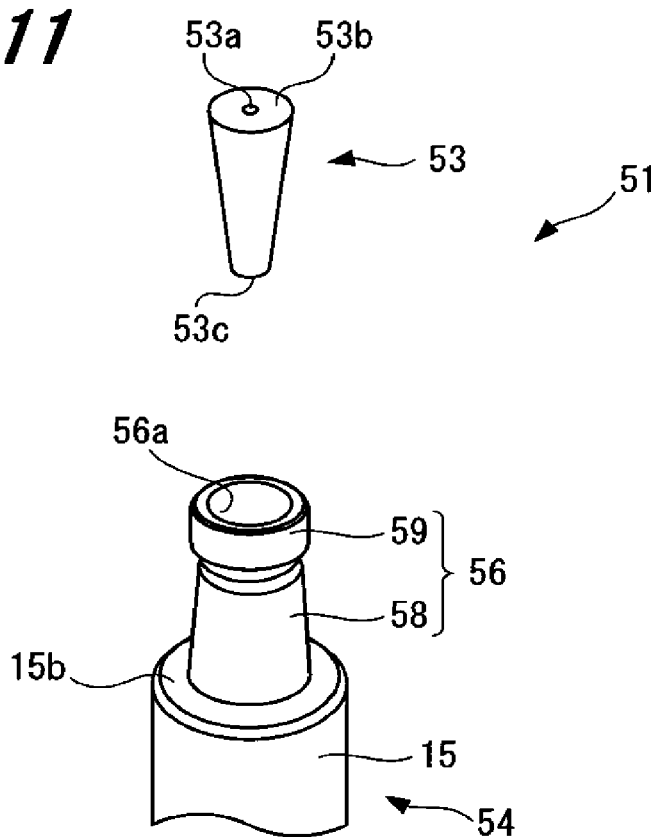
FIG. 11 is an explanatory drawing of a needle-equipped outer tube according to a third embodiment.

Next, a third embodiment of the needle-equipped outer tube is described referring to FIG. 11.

FIG. 11 is an explanatory drawing explaining the third embodiment of the needle-equipped outer tube.

A needle-equipped outer tube 51 which is the third embodiment has a configuration similar to that of the needle-equipped outer tube 31 of the second embodiment (see FIG. 8). The needle-equipped outer tube 51 is different from the needle-equipped outer tube 31 in the shape of a joint member 53 and the shape of a connection section 56 of an outer tube 54.

[Joint Member]

As illustrated in FIG. 11, the joint member 53 is formed in a truncated conical shape and includes a tubular hole (needle insertion hole) 53a in which the needle 2 is inserted. The diameter of the tubular hole 53a is larger than the outer diameter of the needle 2 by about 0.01 to 0.08 mm, preferably, by about 0.01 to 0.03 mm. The plane surface of the joint member 53 having larger diameter is referred to as a distal end surface 53b and the plane surface having smaller diameter is referred to as a rear end surface 53c. The distal end surface 53b is a press force receiving surface which is pressed by the pressing portion 101a (see FIG. 11) of the pressing apparatus 101.

As a material of the joint member 53, a resin similar to that used for the joint member 3 according to the first and second embodiments is preferably used. Further, it is preferable that the material of the joint member 53 is substantially transparent so that the inside of the joint member 53 is visible.

[Outer Tube]

The outer tube 54 includes the outer tube body 15 in which a medicine is filled and a connection section 56 to which the joint member 53 is joined. The connection section 56 is configured with a proximal end side engagement portion 58 which is continued to the end portion 15b of the outer tube body 15 and a distal end side engagement portion 59 which is continued to the proximal end side engagement portion 58.

The proximal end side engagement portion 58 is formed in a truncated conical shape. The diameter of the proximal end side engagement portion 58 gradually decreases toward the distal end side engagement portion 59. Therefore, the proximal end side engagement portion 58 is formed so as that the cross section perpendicular to the axial direction of the outer tube 54 is a near circle.

The distal end side engagement portion 59 is formed in an approximately column shape. The axis of the proximal end side engagement portion 58 and the axis of the distal end side engagement portion 59 are identical to the axis of the outer tube body 15. Further, the cap 5 (see FIG. 4) engages with the distal end side engagement portion 59.

In the connection section 56, an engagement hole 56a which runs throughout the distal end side engagement portion 59 and the proximal end side engagement portion 58 is formed. The engagement hole 56a is formed in a tapered shape (tapered inner shape) having a circular cross section of which diameter gradually decreases toward the end portion 15b of the outer tube body 15. The joint member 53 is inserted in the engagement hole 56a. In this manner, the joint member 53 engages with the connection section 56 via the tapered shape.

The joint member 53 is formed in a tapered shape (tapered outer shape) so as to engage with the engagement hole 56a. Further, taper angles of the engagement hole 56a and the joint member 53 are not particularly limited, though an angle of 1 to 3 degrees is preferable.

Note that, the proximal end side engagement portion 58 of the connection section 56 may include the needle stopping portion 21 (see FIG. 6) thereinside. By providing the needle stopping portion 21 inside the proximal end side engagement portion 58, the needle 2 is positioned against the joint member 53 and the outer tube 54, and the proximal end 2b of the needle 2 is arranged in the connection section 56. As a result, the dead volume in the outer tube 54 can be reduced, thereby reducing the amount of medicine remaining in the outer tube 54.

As a material of the outer tube 54 configured with the connection section 56 and the outer tube body 15, a resin similar to that used for the joint member 53 is preferably used. Further, it is preferable that the material of the outer tube 54 is substantially transparent so that the inside of the outer tube 54 is visible.

Further, the connection section 56 of the outer tube 54 and the joint member 53 are joined by thermal welding. Therefore, it is preferable that the material of the outer tube 54 is substantially the same as the material of the joint member 53. In this manner, preferable bondability between the connection section 56 and the joint member 53 can be obtained so that the connection section 56 and the joint member 53 can firmly be fixed. Further, the welded portion between the connection section 56 and the joint member 53 can be made inconspicuous so that aesthetic of the needle-equipped outer tube 51 can be improved.

The needle-equipped outer tube 51 having the configuration as described above can be manufactured using either the method for manufacturing described in the first embodiment or the method for manufacturing described in the second embodiment. Consequently, the needle 2 (not shown in the drawing) can be fixed to the outer tube 54 without using an adhesive.

Further, since the thermal welding is carried out with the distal end surface 53b of the joint member 53 pressed along the axial direction of the outer tube 54 by the pressing apparatus 101, no gap is produced between the joint member 53 and the connection section 56 of the outer tube 54. Therefore, foaming does not occur in the joint member 53 when the joint member 53 is heated. As a result, transparency is provided to the joint section without deteriorating aesthetic, and at the same time, the joint member 53 and the needle 2 (not shown in the drawing) as well as the joint member 53 and the connection section 56 of the outer tube 54 can tightly be fixed.

4. Fourth Embodiment of the Needle-Equipped Outer Tube

<Configuration of a Needle-Equipped Outer Tube>

Next, the fourth embodiment of the needle-equipped outer tube will be described referring to FIG. 12.

Figure 12:
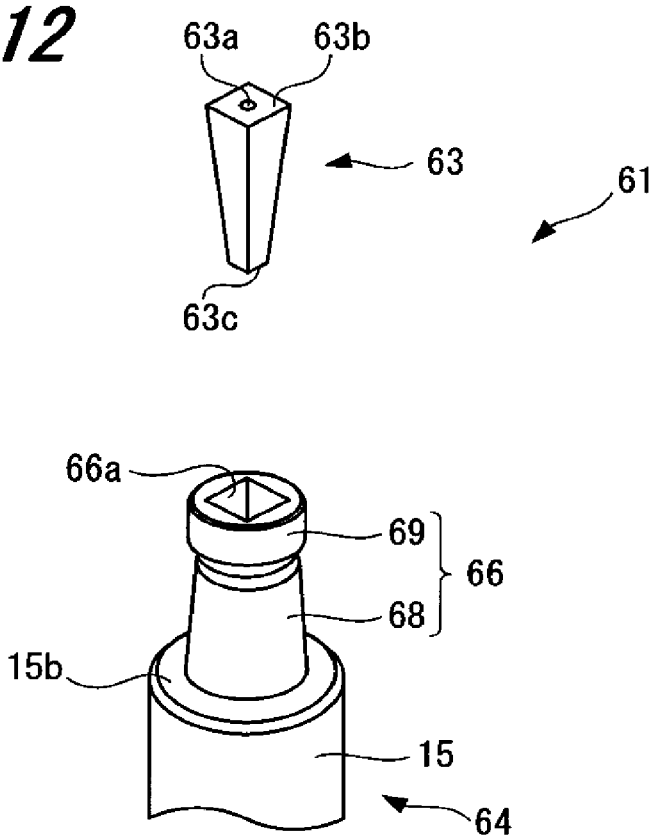
FIG. 12 is an explanatory drawing of a needle-equipped outer tube according to a fourth embodiment.

FIG. 12 is an explanatory drawing of the fourth embodiment of the needle-equipped outer tube.

A needle-equipped outer tube 61 which is the fourth embodiment has a configuration similar to that of the needle-equipped outer tube 31 of the second embodiment (see FIG. 8). The needle-equipped outer tube 61 is different from the needle-equipped outer tube 31 in the shape of a joint member 63 and the shape of a connection section 66 of an outer tube 64.

[Joint Member]

As illustrated in FIG. 12, the joint member 63 is formed in a truncated quadrangular pyramid and includes a tubular hole (needle insertion hole) 63a in which the needle 2 is inserted. The diameter of the tubular hole 63a is larger than the outer diameter of the needle 2 by about 0.01 to 0.08 mm, preferably, by about 0.01 to 0.03 mm. The plane surface of the joint member 63 having larger area is referred to as a distal end surface 63b, and the plane surface having smaller area is referred to as a rear end surface 63c. The distal end surface 63b is a press force receiving surface which is pressed by the pressing portion 101a (see FIG. 11) of the pressing apparatus 101.

As a material of the joint member 63, a resin similar to that used for the joint member 3 according to the first and second embodiments is preferably used. Further, it is preferable that the material of the joint member 63 is substantially transparent so that the inside of the joint member 63 is visible.

[Outer Tube]

The outer tube 64 includes the outer tube body 15 in which a medicine is filled and a connection section 66 to which the joint member 63 is joined. The connection section 66 is configured with a proximal end side engagement portion 68 which is continued to the end portion 15b of the outer tube body 15 and a distal end side engagement portion 69 which is continued to the proximal end side engagement portion 68.

The proximal end side engagement portion 68 is formed in a truncated conical shape. The diameter of the proximal end side engagement portion 68 gradually decreases toward the distal end side engagement portion 69. Therefore, the proximal end side engagement portion 68 is formed so as that the cross section perpendicular to the axial direction of the outer tube 64 is a near circle. Note that, the proximal end side engagement portion 68 may include the needle stopping portion 21 (see FIG. 6) thereinside.

The distal end side engagement portion 69 is formed in an approximately column shape. The axis of the proximal end side engagement portion 68 and the axis of the distal end side engagement portion 69 are identical to the axis of the outer tube body 15. Further, the cap 5 (see FIG. 4) engages with the distal end side engagement portion 69.

In the connection section 66, an engagement hole 66a which runs throughout the distal end side engagement portion 69 and the proximal end side engagement portion 68 is formed. The engagement hole 66a is formed in a tapered shape (tapered inner shape) having a rectangular cross section of which contour gradually decreases toward the end portion 15b of the outer tube body 15. The joint member 63 is inserted in the engagement hole 66a. In this manner, the joint member 63 engages with the connection section 66 via the tapered shape.

The joint member 63 is formed in a tapered shape (tapered outer shape) so as to engage with the engagement hole 66a. Further, taper angles of the engagement hole 66a and the joint member 63 are not particularly limited, though an angle of 1 to 3 degrees is preferable.

As a material of the outer tube 54 configured with the connection section 66 and the outer tube body 15, a resin similar to that used for the joint member 63 is preferably used. Note that, it is preferable that the material of the outer tube 64 is substantially transparent so that the inside of the outer tube 64 is visible. Further, the connection section 66 of the outer tube 64 and the joint member 63 are joined by thermal welding. Therefore, it is preferable that the material of the outer tube 64 is substantially the same as the material of the joint member 63.

The needle-equipped outer tube 61 having the configuration as described above can be manufactured using either the method for manufacturing described in the first embodiment or the method for manufacturing described in the second embodiment. As a result, the needle 2 (not shown in the drawing) is fixed to the outer tube 64 without using an adhesive.

Further, since the thermal welding is carried out with the distal end surface 63b of the joint member 63 pressed along the axial direction of the outer tube 64 by the pressing apparatus 101, no gap is produced between the joint member 63 and the connection section 66 of the outer tube 64. Therefore, foaming does not occur in the joint member 63 when the joint member 63 is heated. As a result, transparency is provided to the joint section without deteriorating aesthetic, and at the same time, the joint member 63 and the needle 2 (not shown in the drawing) as well as the joint member 63 and the connection section 66 of the outer tube 64 can tightly be fixed.

5. Fifth Embodiment of the Needle-Equipped Outer Tube

<Configuration of a Needle-Equipped Outer Tube>

Figure 13:
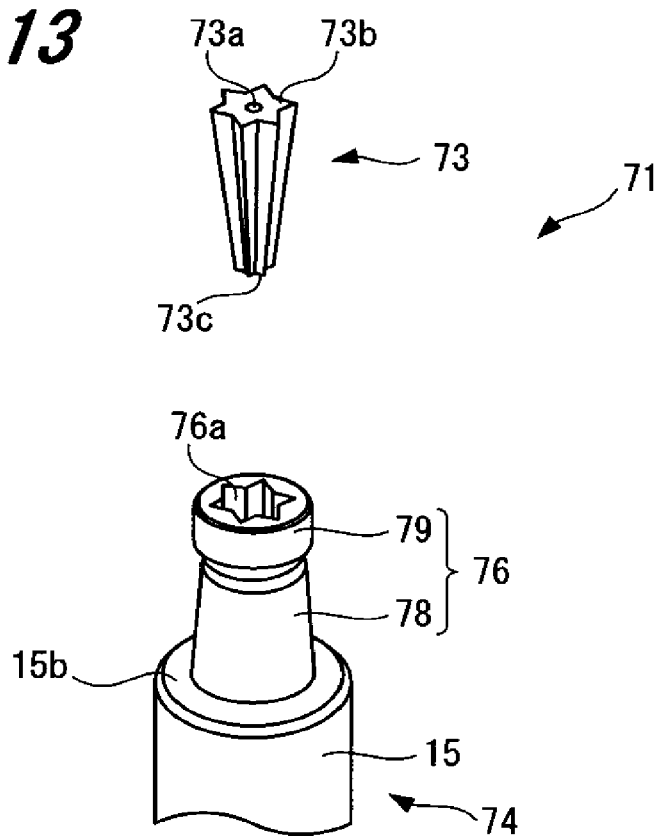
FIG. 13 is an explanatory drawing of a needle-equipped outer tube according to a fifth embodiment.

Now, the fifth embodiment of the needle-equipped outer tube will be described referring to FIG. 13. FIG. 13 is an explanatory drawing of the fifth embodiment of the needle-equipped outer tube.

A needle-equipped outer tube 71 which is the fifth embodiment has a configuration similar to that of the needle-equipped outer tube 31 of the second embodiment (see FIG. 8). The needle-equipped outer tube 71 is different from the needle-equipped outer tube 31 in the shape of a joint member 73 and the shape of a connection section 76 of an outer tube 74.

[Joint Member]

As illustrated in FIG. 13, the joint member 73 is formed in a polygonal columnar shape so as to have a hexagram cross section in a direction perpendicular to the axial direction. The joint member 73 includes a tubular hole (needle insertion hole) 73a in which the needle 2 (not shown in the drawing) is inserted. The diameter of the tubular hole 73a is larger than the outer diameter of the needle 2 by about 0.01 to 0.08 mm, preferably, by about 0.01 to 0.03 mm.

The joint member 73 is formed in a tapered shape of which contour gradually decreases from the end portion toward the other end portion along the axial direction. The plane surface of the joint member 73 on the end along the axial direction having larger area is referred to as a distal end surface 73b, and the plane surface on the other end having smaller area is referred to as a rear end surface 73c. The distal end surface 73b is a press force receiving surface which is pressed by the pressing portion 101a (see FIG. 11) of the pressing apparatus 101.

As a material of the joint member 73, a resin similar to that used for the joint member 3 according to the first and second embodiments is preferably used. Further, it is preferable that the material of the joint member 73 is substantially transparent so that the inside of the joint member 73 is visible.

[Outer Tube]

The outer tube 74 includes the outer tube body 15 in which a medicine is filled and the connection section 76 to which the joint member 73 is joined. The connection section 76 is configured with a proximal end side engagement portion 78 which is continued to the end portion 15b of the outer tube body 15 and a distal end side engagement portion 79 which is continued to the proximal end side engagement portion 78.

The proximal end side engagement portion 78 is formed in a truncated conical shape. The diameter of the proximal end side engagement portion 78 gradually decreases toward the distal end side engagement portion 79. Therefore, the proximal end side engagement portion 78 is formed so as that the cross section perpendicular to the axial direction of the outer tube 74 is a near circle. Note that, the proximal end side engagement portion 78 may include the needle stopping portion 21 (see FIG. 6) thereinside.

The distal end side engagement portion 79 is formed in an approximately column shape. The axis of the proximal end side engagement portion 78 and the axis of the distal end side engagement portion 79 are identical to the axis of the outer tube body 15. Further, the cap 5 (see FIG. 4) engages with the distal end side engagement portion 79.

In the connection section 76, an engagement hole 76a which runs throughout the distal end side engagement portion 79 and the proximal end side engagement portion 78 is formed. The engagement hole 76a is formed in a tapered shape (tapered inner shape) having a hexagram cross section of which contour gradually decreases toward the end portion 15b of the outer tube body 15. The joint member 73 is inserted in the engagement hole 76a. In this manner, the joint member 73 engages with the connection section 76 via the tapered shape.

The joint member 73 is formed in a tapered shape (tapered outer shape) so as to engage with the engagement hole 76a. Further, taper angles of the engagement hole 76a and the joint member 73 are not particularly limited, though an angle of 1 to 3 degrees is preferable.

As a material of the outer tube 74 configured with the connection section 76 and the outer tube body 15, a resin similar to that used for the joint member 73 is preferably used. Note that, it is preferable that the material of the outer tube 74 is substantially transparent so that the inside of the outer tube 74 is visible. Further, the connection section 76 of the outer tube 74 and the joint member 73 are joined by thermal welding. Therefore, it is preferable that the material of the outer tube 74 is substantially the same as the material of the joint member 73.

The needle-equipped outer tube 71 having the configuration as described above can be manufactured using either the method for manufacturing described in the first embodiment or the method for manufacturing described in the second embodiment. As a result, the needle 2 (not shown in the drawing) is fixed to the outer tube 74 without using an adhesive.

Further, since the thermal welding is carried out with the distal end surface 73b of the joint member 73 pressed along the axial direction of the outer tube 74 by the pressing apparatus 101, no gap is produced between the joint member 73 and the connection section 76 of the outer tube 74. Therefore, foaming does not occur in the joint member 73 when the joint member 73 is heated. As a result, transparency is provided to the joint section without deteriorating aesthetic, and at the same time, the joint member 73 and the needle 2 (not shown in the drawing) as well as the joint member 73 and the connection section 76 of the outer tube 74 can tightly be fixed.

6. Sixth Embodiment of the Needle-Equipped Outer Tube

<Configuration of a Needle-Equipped Outer Tube>

Next, the sixth embodiment of the needle-equipped outer tube will be described referring to FIG. 14.

Figure 14:
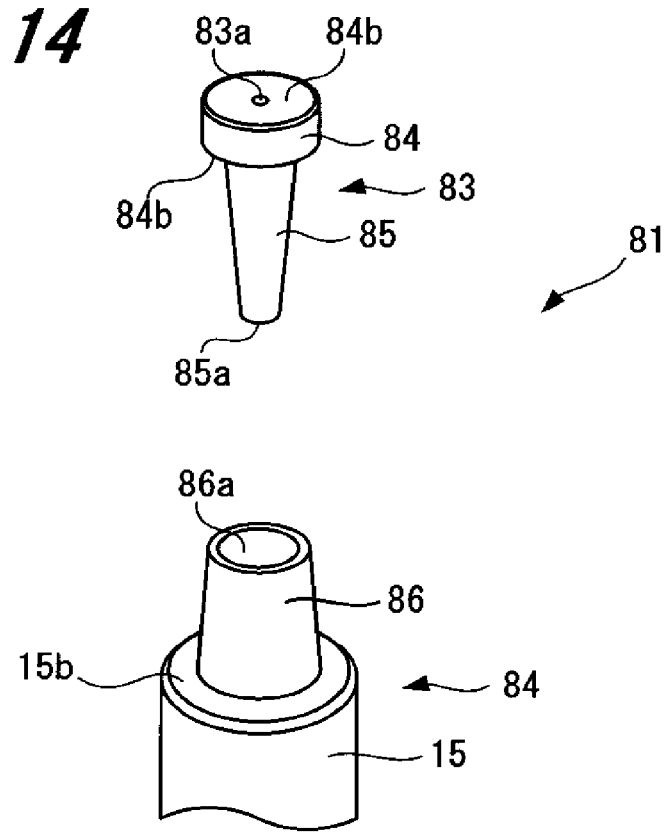
FIG. 14 is an explanatory drawing of a needle-equipped outer tube according to a sixth embodiment.

FIG. 14 is an explanatory drawing of the sixth embodiment of the needle-equipped outer tube.

A needle-equipped outer tube 81 which is the sixth embodiment has a configuration similar to that of the needle-equipped outer tube 31 of the second embodiment (see FIG. 8). The needle-equipped outer tube 81 is different from the needle-equipped outer tube 31 in the shape of a joint member 83 and the shape of a connection section 86 of an outer tube 84.

[Joint Member]

As illustrated in FIG. 14, the joint member 83 is formed in an approximately cylindrical shape having a tubular hole (needle insertion hole) 83a in which the needle 2 is inserted. The diameter of the tubular hole 83a is larger than the outer diameter of the needle 2 (not shown in the drawing) by about 0.01 to 0.08 mm, preferably, by about 0.01 to 0.03 mm.

The joint member 83 is configured with a distal end side tubular portion 84 and a rear end side tubular portion 85 having an outer diameter smaller than that of the distal end side tubular portion 84. The distal end side tubular portion 84 is formed in a cylindrical shape having a uniform outer diameter.

On the end portion, opposite to the rear end side tubular portion 85, of the distal end side tubular portion 84, a distal end surface 84a is formed. The distal end surface 84a is a press force receiving surface which is pressed by the pressing portion 101a of the pressing apparatus 101 which will be described below. On the end portion, opposite to the rear end side tubular portion 84, of the distal end side tubular portion 84, a contact surface 84b is formed. The contact surface 84b makes contact with the connection section 86 of the outer tube 84. Further, the cap 5 (see FIG. 4) engages with the distal end side engagement portion 84.

The rear end side tubular portion 85 is formed in a truncated conical shape. The diameter of the rear end side tubular portion 85 gradually decreases toward the end portion opposite to the distal end side tubular portion 84. Further, on the end portion, opposite to the distal end side tubular portion 84, of the rear end side tubular portion 85, a rear end surface 85a is formed.

As a material of the joint member 83, a resin similar to that used for the joint member 3 according to the first and second embodiments is preferably used. Further, it is preferable that the material of the joint member 83 is substantially transparent so that the inside of the joint member 83 is visible.

[Outer Tube]

The outer tube 84 includes the outer tube body 15 in which a medicine is filled and a connection section 86 to which the joint member 83 is joined. The connection section 86 is continued to the end portion 15b of the outer tube body 15.

The connection section 86 is formed, similarly to the tapered engagement portion 48 (see FIG. 8) of the connection section 46 according to the second embodiment, in a truncated conical shape. The diameter of the connection section 86 gradually decreases toward the distal end side engagement portion 19.

The connection section 86 includes an engagement hole 86a. The engagement hole 86a is formed in a tapered shape (tapered inner shape) in which the diameter gradually decreases toward the end portion 15b of the outer tube body 15. The rear end side tubular portion 85 of the joint member 83 is inserted in the engagement hole 86a. In this manner, the rear end side tubular portion 85 of the joint member 83 engages with the connection section 86 via the tapered shape. Note that, the connection section 86 may include the needle stopping portion 21 (see FIG. 6) thereinside.

The rear end side tubular portion 85 of the joint member 83 is formed in a tapered shape (tapered outer shape) so as to engage with the engagement hole 86a. Further, taper angles of the engagement hole 86a and the rear end side tubular portion 85 are not particularly limited, though an angle of 1 to 3 degrees is preferable.

As a material of the outer tube 84 configured with the connection section 86 and the outer tube body 15, a resin similar to that used for the joint member 83 is preferably used. Note that, it is preferable that the material of the outer tube 84 is substantially transparent so that the inside of the outer tube 84 is visible. Further, the connection section 86 of the outer tube 84 and the rear end side tubular portion 85 of the joint member 83 are joined by thermal welding. Therefore, it is preferable that the material of the outer tube 84 is substantially the same as the material of the joint member 83.

The needle-equipped outer tube 81 having the configuration as described above can be manufactured using either the method for manufacturing described in the first embodiment or the method for manufacturing described in the second embodiment. As a result, the needle 2 (not shown in the drawing) is fixed to the outer tube 84 without using an adhesive.

Further, since the thermal welding is carried out with the distal end surface 84*a* of the joint member 83 pressed along the axial direction of the outer tube 84 by the pressing apparatus 101, no gap is produced between the rear end side tubular portion 85 of the joint member 83 and the connection section 86 of the outer tube 84. Therefore, foaming does not occur in the rear end side tubular portion 85 when the rear end side tubular portion 85 of the joint member 83 is heated. As a result, transparency is provided to the joint section without deteriorating aesthetic, and at the same time, the joint member 83 and the needle 2 (not shown in the drawing) as well as the rear end side tubular portion 85 of the joint member 83 and the connection section 86 of the outer tube 84 can tightly be fixed.

7. Seventh Embodiment of the Needle-Equipped Outer Tube

<Configuration of a Needle-Equipped Outer Tube>

Next, the seventh embodiment of the needle-equipped outer tube will be described referring to FIG. 15.

Figure 15:
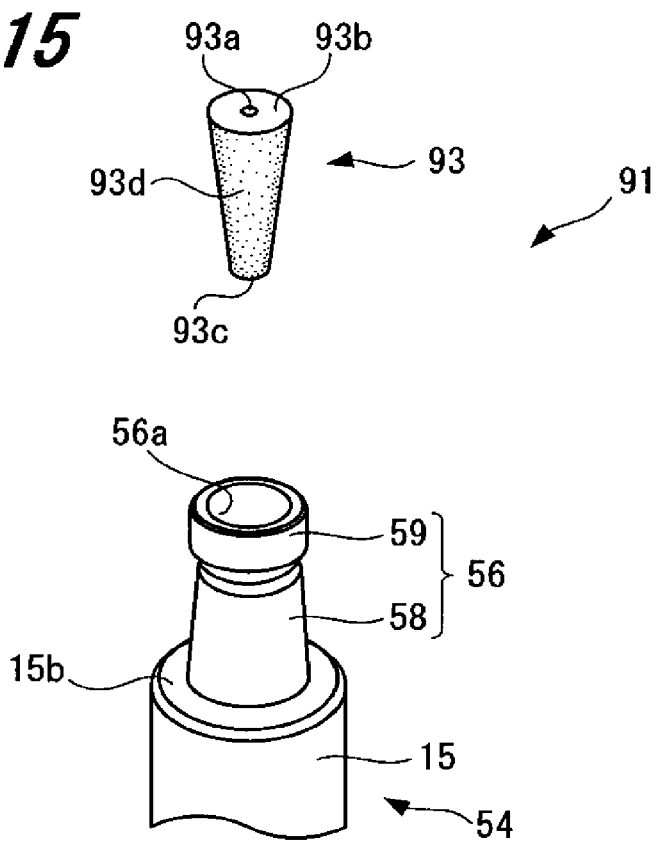
FIG. 15 is an explanatory drawing of a needle-equipped outer tube according to a seventh embodiment.

FIG. 15 is an explanatory drawing of the seventh embodiment of the needle-equipped outer tube.

A needle-equipped outer tube 91 which is the seventh embodiment has a configuration similar to that of the needle-equipped outer tube 51 of the third embodiment (see FIG. 11). The needle-equipped outer tube 91 is different from the needle-equipped outer tube 51, solely, in the shape of a joint member 93.

As illustrated in FIG. 15, the joint member 93 of the needle-equipped outer tube 91 is formed, similarly to the joint member 53 according to the third embodiment, in a truncated conical shape. The joint member 93 includes a tubular hole 93*a*, a distal end surface 93*b*, a rear end surface 93*c*, and an outer circumferential surface 93*d*.

Further, substantially same transparent materials are used for materials of the joint member 93 and the outer tube 54.

Roughening process is applied to the outer circumferential surface 93*d* of the joint member 93.

As the method of roughening process applied to the outer circumferential surface of the joint member 93, for example, a method of transferring the roughness provided on a mold for forming the joint member 93 may be used. Further, blasting may be applied after forming the joint member 93 having a smooth outer circumferential surface. Further, the roughness of the outer circumferential surface of the joint member 93, after roughening process is applied, is preferably, for example, Ra 0.1 to 3. Further, satin process or embossing process may be applied to the outer circumferential surface 93*d* of the joint member 93.

The needle-equipped outer tube 91 having the configuration as described above can be manufactured using either the method for manufacturing described in the first embodiment or the method for manufacturing described in the second embodiment. Consequently, the needle 2 (not shown in the drawing) can be fixed to the outer tube 54 without using an adhesive.

Further, since the thermal welding is carried out with the distal end surface 93*a* of the joint member 93 pressed along the axial direction of the outer tube 54 by the pressing apparatus 101, no gap is produced between the joint member 93 and the connection section 56 of the outer tube 54. Therefore, foaming does not occur in the joint member 93 when the joint member 93 is heated. As a result, transparency is provided to the joint section without deteriorating aesthetic, and at the same time, the joint member 93 and the needle 2 (not shown in the drawing) as well as the joint member 93 and the connection section 56 of the outer tube 54 can tightly be fixed.

Further, as for the joint section between the joint member 93 and the connection section 56, the welded portion becomes transparent and the portion which is not welded becomes nontransparent. Therefore, it can easily be recognized whether the welded state between the joint member 93 and the connection section 56 is good.

In the embodiment, roughening process is applied to the outer circumferential surface of the joint member 93. However, roughening process can be applied to the inner circumferential surface of the connection section 53 to manufacture the needle-equipped outer tube of the present invention. Further, the roughening process applied in the embodiment can be applied in the first, second, and fourth to sixth embodiments described above.

The present invention is not limited to the embodiments described above and illustrated in the drawings. Various modifications can be made without departing from the spirit and the scope of the present invention described in the claims.

For example, in the first and second embodiments described above, high frequency welding and laser welding are applied as specific examples of thermal welding, though ultrasonic welding can be applied as the thermal welding according to embodiments of the present invention.

Further, the outer tube 4 of the first embodiment described above can be replaced with the outer tube 34 of the second embodiment described above. Similarly, the outer tube 34 of the second embodiment can be replaced with the outer tube 4 of the first embodiment.

Further, in the first embodiment described above, the cross section of the tapered engagement portion 18 of the connection section 16 is formed in an approximate cross-shape, and in the second to seventh embodiments described above, the cross section of the tapered engagement portion of the connection section is formed in a near circle (approximately cylindrical shape). However, the cross section of the connection section according to the present invention may be a polygon such as a triangle and a rectangle, or may be other shapes such as an ellipse and a half circle.

Further, in the first to seventh embodiments described above, the joint member is configured to engage with the connection section via the tapered shape. However, in the method for manufacturing the needle-equipped outer tube of the present invention, it is not limited to the engagement via the tapered shape as long as the joint member and the connection section engage with each other during thermal welding. Note that, it is effective to engage the joint member and the connection section via the tapered shape, in that a gap (clearance) between the joint member and the connection section can be eliminated or made small, thereby preventing foaming during the thermal welding.

Further, in the first to seventh embodiments described above, the shape of the joint member is formed in a truncated conical shape, a truncated quadrangular pyramid, or a polygonal columnar shape (hexagram). However, the shape of the joint member according to embodiments of the present invention may suitably be modified as long as the shape allows joining to the connection section.

What is claimed is:

1. A needle-equipped outer tube comprising:
  a needle;
  a transparent joint member that supports the needle, the needle being insert molded or thermally welded to the transparent joint member; and
  a transparent outer tube including a connection section,
  wherein the transparent joint member is thermally welded to the connection section of the transparent outer tube at a thermally welded portion such that a uniform and transparent boundary surface is formed between the transparent joint member and the connection section without foaming at the thermally welded portion.

2. The needle-equipped outer tube according to claim 1, wherein a connection between the transparent joint member and the connection section is a connection formed by thermally welding the transparent joint member to the connection section while the transparent joint member is pressed against the connection section in an axial direction of the transparent outer tube.

3. The needle-equipped outer tube according to claim 2, wherein the transparent joint member includes a press force receiving surface from which the needle protrudes, the press force receiving surface being configured to be pressed during said thermal welding.

4. The needle-equipped outer tube according to claim 1, wherein a first end portion of the needle is arranged in the connection section of the transparent outer tube.

5. The needle-equipped outer tube according to claim 1, wherein a material of which the joint member is formed is substantially the same as a material of which the outer tube is formed.

6. The needle-equipped outer tube according to claim 5, wherein the material of which the joint member is formed is the same as the material of which the outer tube is formed.

7. The needle-equipped outer tube according to claim 6, wherein the joint member and the outer tube each comprise a cyclic polyolefin material.

* * * * *